(12) United States Patent
Lim et al.

(10) Patent No.: US 11,345,647 B2
(45) Date of Patent: May 31, 2022

(54) PROCESS FOR PRODUCING 1,1,2-TRICHLOROETHANE

(71) Applicant: Hanwha Solutions Corporation, Seoul (KR)

(72) Inventors: Dong Wook Lim, Daejeon (KR); Shin Beom Lee, Daejeon (KR); Jung Hun Kim, Seongnam-si (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 0 days.

(21) Appl. No.: 16/649,229

(22) PCT Filed: Sep. 11, 2018

(86) PCT No.: PCT/KR2018/010631
§ 371 (c)(1),
(2) Date: Mar. 20, 2020

(87) PCT Pub. No.: WO2019/066311
PCT Pub. Date: Apr. 4, 2019

(65) Prior Publication Data
US 2020/0299213 A1 Sep. 24, 2020

(30) Foreign Application Priority Data
Sep. 27, 2017 (KR) .................. 10-2017-0125450

(51) Int. Cl.
*C07C 17/04* (2006.01)
*C07C 19/05* (2006.01)
*B01J 19/24* (2006.01)
*B01J 27/128* (2006.01)
*C07C 17/383* (2006.01)

(52) U.S. Cl.
CPC .......... *C07C 17/04* (2013.01); *B01J 19/2435* (2013.01); *B01J 27/128* (2013.01); *C07C 17/383* (2013.01); *C07C 19/05* (2013.01)

(58) Field of Classification Search
CPC ................................... C07C 17/04
See application file for complete search history.

(56) References Cited

U.S. PATENT DOCUMENTS 7,009,084 B2   3/2006  Benje et al.
2005/0177011 A1* 8/2005 Benje .................. C07C 17/02
                                                          570/231

(Continued)

FOREIGN PATENT DOCUMENTS

CN       102249843      11/2011
CN       103819307       5/2014
GB       627263 A    *   8/1949 ............. C07C 17/04

(Continued)

OTHER PUBLICATIONS

English translation of JP4964717B2, Published Jul. 4, 2012, pp. 1-13 (Year: 2012).*

(Continued)

*Primary Examiner* — Medhanit W Bahta
(74) *Attorney, Agent, or Firm* — Lex IP Meister, PLLC

(57) ABSTRACT

The present disclosure relates to a process for producing 1,1,2-trichloroethane. According to the present disclosure, a process for producing 1,1,2-trichloroethane with a simplified equipment and a high reaction yield is provided.

5 Claims, 1 Drawing Sheet

(56) References Cited

U.S. PATENT DOCUMENTS

2008/0125613 A1* 5/2008 Benje .................. B01F 23/2323
422/600
2017/0050904 A1 2/2017 Ondrus et al.

FOREIGN PATENT DOCUMENTS

| JP | 2003-246756 | 9/2003 |
|----|-------------|--------|
| JP | 4964717 | 7/2012 |

OTHER PUBLICATIONS

Joaquin A. Orejas, "Model evaluation for an industrial process of direct chlorination of ethylene in a bubble-column reactor with external recirculation loop", Chemical Engineering Science, 2001, vol. 56, pp. 513-522.

M.E.E. Abashar, "Ethylene Dichloride Production in External-loop Gaslift Reactors", Journal of King Saud University—Engineering Sciences, 2004, vol. 16, No. 2, pp. 179-202.

Joaquin A. Orejas, "Modelling and simulation of a bubble-column reactor with external loop: Application to the direct chlorination of ethylene", Chemical Engineering Science, 1999, vol. 54, pp. 5299-5309.

KIPO, PCT Search Report & Written Opinion of PCT/KR2018/010631 dated Dec. 17, 2018.

* cited by examiner

[FIG. 1]
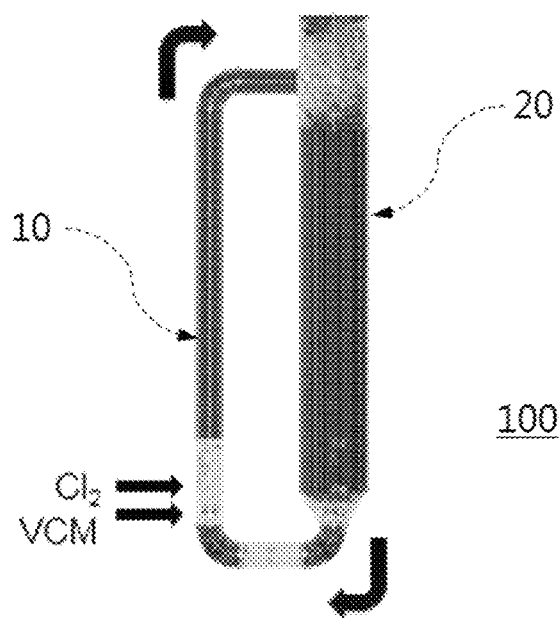
[FIG. 2]
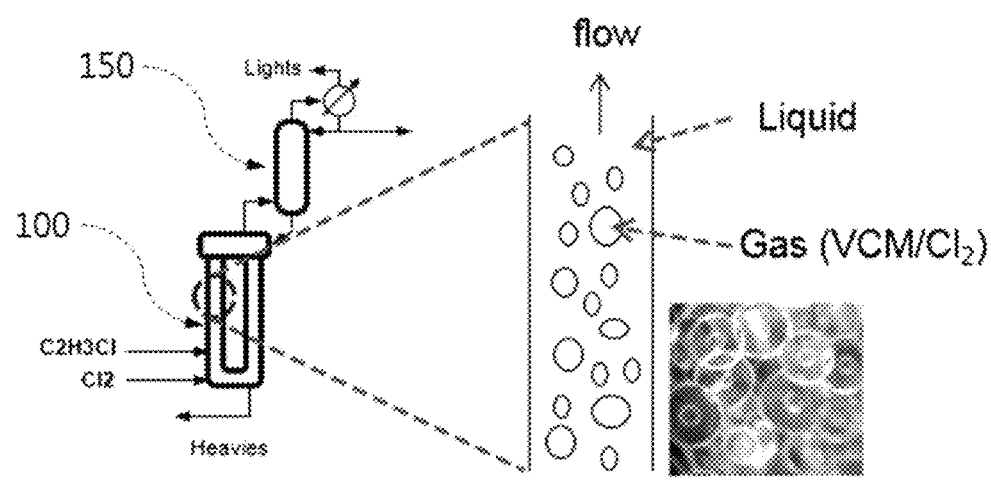

PROCESS FOR PRODUCING 1,1,2-TRICHLOROETHANE

TECHNICAL FIELD

The present disclosure relates to a process for producing 1,1,2-trichloroethane by a chlorine addition reaction of a vinyl chloride monomer.

BACKGROUND OF ART 1,1,2-trichloroethane is an organic chloride represented by the molecular formula $C_2H_3Cl_3$, and is an isomer of 1,1,1-trichloroethane. It is used as a solvent and an intermediate in the synthesis of 1,1-dichloroethane.

1,1,2-trichloroethane is prepared by chlorination of a vinyl chloride monomer. The chlorination of the vinyl chloride monomer is an addition reaction in which chlorine is added to a double bond of the vinyl chloride monomer and very high heat of reaction is generated. Thus, the chlorination of the vinyl chloride monomer is industrially carried out in a low temperature liquid medium.

However, the chlorination of the vinyl chloride monomer requires a fairly long residence time. For example, the chlorination of the vinyl chloride monomer requires about six times longer residence time than the residence time required for chlorination of ethylene. Further, in order to produce the same amount in the same time, the chlorination of the vinyl chloride monomer requires about 6 times larger reaction equipment than the reaction equipment required for the chlorination of ethylene.

DETAILED DESCRIPTION OF THE INVENTION

Technical Problem

The present disclosure is to provide a process for producing 1,1,2-trichloroethane with simplified equipment and a high reaction yield while being able to effectively control the high heat of reaction generated during the chlorination of the vinyl chloride monomer.

Technical Solution

According to an embodiment of the present disclosure, a process for producing 1,1,2-trichloroethane is provided, including a step of obtaining a product containing 1,1,2-trichloroethane by an addition reaction of dissolved a vinyl chloride monomer and dissolved chlorine in contact with each other under a liquid medium including a chlorinated hydrocarbon-based solvent and a catalyst suspended therein, wherein the step is carried out in a reaction unit including a gas-lift type of bubble column through which the liquid medium is circulated by gas containing the dissolved vinyl chloride monomer and dissolved chlorine and an external down-corner which circulates the gas and liquid medium out of the bubble column.

Hereinafter, the process for producing 1,1,2-trichloroethane according to an embodiment of the present disclosure will be described in detail.

The terminology used herein is used merely to refer to specific embodiments, and is not intended to restrict the present disclosure unless that is explicitly expressed.

Singular expressions of the present disclosure may include plural expressions unless they are differently expressed contextually.

The terms "include", "comprise", and the like of the present disclosure are used to specify certain features, regions, integers, steps, operations, elements, and/or components, and these do not exclude the existence or the addition of certain other features, regions, integers, steps, operations, elements, and/or components.

As a result of continuous research by the present inventors, it was found that when the chlorination of a vinyl chloride monomer for the production of 1,1,2-trichloroethane is carried out using a reaction unit including a gas-lift type of bubble column equipped with an external down-corner, it is possible to produce 1,1,2-trichloroethane with simplified equipment and a high reaction yield while being able to effectively control the high heat of reaction.

In particular, the external down-corner of the reaction unit acts as a heat exchanger for circulating the liquid medium including the dissolved reactants out of the bubble column to discharge the heat of reaction of the reaction system, while maintaining sufficient contact and residence time of the reactants required for the chlorination. Thus, it allows for continuous chlorination of the vinyl chloride monomer in its circulation.

Accordingly, the process for producing 1,1,2-trichloroethane of the present disclosure can not only drastically reduce the size of the reaction equipment as compared to a process using a cylindrical bubble column with a conventional vertical axis, but can also provide 1,1,2-trichloroethane with a continuous and high reaction yield.

According to an embodiment of the present disclosure, a process for producing 1,1,2-trichloroethane is provided, including a step of obtaining a product containing 1,1,2-trichloroethane by an addition reaction of a dissolved vinyl chloride monomer and dissolved chlorine in contact with each other under a liquid medium including a chlorinated hydrocarbon-based solvent and a catalyst suspended therein, wherein the step is carried out in a reaction unit including a gas-lift type of bubble column through which the liquid medium is circulated by gas containing the dissolved vinyl chloride monomer and dissolved chlorine and an external down-corner which circulates the gas and liquid medium out of the bubble column.

According to an embodiment of the present disclosure, the desired product, 1,1,2-trichloroethane, is prepared by chlorination of the vinyl chloride monomer.

The chlorination of the vinyl chloride monomer is an addition reaction where chlorine is added to a double bond of the vinyl chloride monomer and very high heat of reaction ($\Delta H=-224$ kJ/mol) is generated.

In this embodiment, it is advantageous for the control of the heat of reaction that the chlorination of the vinyl chloride monomer is carried out in a liquid medium.

Herein, a medium having high solubility of two reactant gases (i.e., the vinyl chloride monomer and chlorine) used for the chlorination and capable of easily recovering a desired product may be used as the liquid medium.

Specifically, the liquid medium preferably includes a chlorinated hydrocarbon-based solvent. The chlorinated hydrocarbon-based solvent may be at least one compound selected from the group consisting of carbon tetrachloride, chloroform, 1,2-dichloroethane, methylene chloride, trichloroethylene, 1,1,1-trichloroethane, 1,1,2-trichloroethane, and tetrachloroethylene. 1,2-dichloroethane and 1,1,2-trichloroethane may be more preferably used as the solvent. Most preferably, 1,1,2-trichloroethane may be advantageous for the recovery of the desired product.

In addition, the liquid medium includes a catalyst suspended in the solvent.

That is, the chlorination of the vinyl chloride monomer is carried out under a liquid medium in which catalyst particles are dispersed in the solvent.

The catalyst may be used without particular limitation as long as it is known as a catalyst suitable for the chlorine addition reaction in the art. For example, the catalyst may preferably be iron(III) chloride.

A concentration of the catalyst included in the liquid medium may be determined within a conventional range in consideration of the size of the reaction and reaction efficiency. For example, the catalyst may be included at 50 ppm or more, 100 ppm or more, or 150 ppm or more; and 1000 ppm or less, 900 ppm or less, or 800 ppm or less. Preferably, the catalyst may be included in the range of 100 ppm to 1000 ppm.

Preferably, the step of obtaining a product containing 1,1,2-trichloroethane is carried out by an addition reaction of the dissolved vinyl chloride monomer and dissolved chlorine in contact with each other under a liquid medium including a chlorinated hydrocarbon-based solvent and a catalyst suspended therein.

The chlorination of vinyl chloride monomer proceeds by contacting two reactant gases dissolved in the liquid medium. That is, the two reactant gases are fed to the liquid medium to form a number of bubbles, and the chlorination proceeds in each bubble. The liquid 1,1,2-trichloroethane produced by the chlorination is dissolved in the liquid medium and circulated. Remaining reactant gases are dissolved and circulated in the liquid medium due to their high solubility, and may be further reacted by the contact occurring during the circulating process.

The chlorination of the vinyl chloride monomer is an exothermic reaction generating very high heat of reaction. Therefore, the step of obtaining the product containing 1,1,2-trichloroethane is preferably carried out at a low temperature, which is advantageous for controlling the heat of reaction.

For example, the step of obtaining the product containing 1,1,2-trichloroethane may be carried out at a reaction temperature of 25 to 80° C. Specifically, the step may be carried out at a reaction temperature of 80° C. or less, 70° C. or less, 60° C. or less, 50° C. or less, or 40° C. or less; and 25° C. or higher, 30° C. or higher, or 35° C. or higher.

In particular, according to an embodiment of the present disclosure, the step of obtaining the product containing 1,1,2-trichloroethane may be carried out in a reaction unit including a gas-lift type of bubble column through which the liquid medium is circulated by gas containing the dissolved vinyl chloride monomer and dissolved chlorine and an external down-corner which circulates the gas and liquid medium out of the bubble column.

FIG. 1 schematically shows an example of the reaction unit according to an embodiment of the present disclosure.

Referring to FIG. 1, the gas-lift type of bubble column 10 and the external down-corner 20 are connected to each other to form a loop for communication.

In the gas-lift type of bubble column 10, a main reaction of the dissolved vinyl chloride monomer and dissolved chlorine proceeds. The external down-corner 20 is a heat exchanger configured to circulate the liquid medium including the dissolved reactants (dissolved vinyl chloride monomer and dissolved chlorine) out of the bubble column 10 to discharge the heat of reaction of the reaction system. In this case, the liquid medium circulates the loop by the gas containing the dissolved reactants without a separate pump. If necessary, an inert gas such as nitrogen or air may be injected in addition to the dissolved reactants to circulate the liquid medium.

In particular, the external down-corner 20 ensures sufficient contact and residence time of the reactants required for the chlorination of the vinyl chloride monomer, while acting as a heat exchanger for discharging the heat of reaction generated by the main reaction to the outside. Accordingly, the chlorination of the vinyl chloride monomer may be continuously performed while the liquid medium including the dissolved reactants circulates through the external down-corner 20.

According to an embodiment of the present disclosure, the bubble column 10 is provided with a nozzle for supplying the vinyl chloride monomer and chlorine. Preferably, in order to smoothly circulate the liquid medium and improve the reaction efficiency of the chlorination, the vinyl chloride monomer and chlorine may be respectively supplied to a section in which the liquid medium rises in the bubble column 10. The vinyl chloride monomer and chlorine may be supplied through separate nozzles or one nozzle.

Herein, the vinyl chloride monomer and chlorine may be supplied at a volumetric flow rate ratio of 1:1 to 1:0.8, which may be advantageous for improving the reaction efficiency. For example, the vinyl chloride monomer and chlorine may be continuously added at an SLPM (standard liter per minute) ratio of 1:1 to 1:0.8. The SLPM represents a volume of gas in the standard state (0° C. and 1 atmosphere) in liters.

Remaining chlorine in the chlorination of vinyl chloride monomer may act as a factor for lowering selectivity of the reaction by further chlorinating the desired product, 1,1,2-trichloroethane. Therefore, the vinyl chloride monomer is preferably added in excess relative to chlorine in order to minimize the amount of residual chlorine.

According to an embodiment of the present disclosure, the process for producing 1,1,2-trichloroethane may further include a step of recovering 1,1,2-trichloroethane by distilling the product containing the 1,1,2-trichloroethane.

FIG. 2 schematically shows another example of the reaction unit according to an embodiment of the present disclosure.

Referring to FIG. 2, after sufficient chlorination of vinyl chloride monomer proceeds in the reaction unit 100, a product containing 1,1,2-trichloroethane may be obtained from one side of the gas-lift type of bubble column 10, and the product may be supplied to a distillation column 150 to selectively recover 1,1,2-trichloroethane by distillation.

As described above, the process for producing 1,1,2-trichloroethane of the present disclosure performs the chlorination of the vinyl chloride monomer using a reaction unit including a gas-lift type of bubble column equipped with an external down-corner.

Accordingly, the process can not only drastically reduce the size of the reaction equipment to about ⅙ as compared to a process using a cylindrical bubble column with a conventional vertical axis, but also provide 1,1,2-trichloroethane with a continuous and high reaction yield.

Advantageous Effects

According to the present disclosure, a process for producing 1,1,2-trichloroethane with a simplified equipment and a high reaction yield while being able to effectively control the high heat of reaction generated during the chlorination of vinyl chloride monomer is provided.

BRIEF DESCRIPTION OF THE DRAWINGS

FIG. 1 schematically shows an example of a reaction unit used in the process for producing 1,1,2-trichloroethane according to an embodiment of the present disclosure.

FIG. 2 schematically shows another example of a reaction unit used in the process for producing 1,1,2-trichloroethane according to an embodiment of the present disclosure.

DETAILED DESCRIPTION OF THE EMBODIMENTS

Hereinafter, preferable examples and comparative examples are presented for better understanding the present invention. However, the following examples are only for illustrating the present invention and the present invention is not limited to or by them.

Example

A gas-lift type of bubble column (capacity 20 L) equipped with an external down-corner as shown in FIG. 1 was prepared.

About 16.5 L of 1,2-dichloroethane, which is a liquid medium, and 100 ppm of iron(III) chloride were added to the bubble column and the external down-corner.

The vinyl chloride monomer and chlorine were continuously supplied at 8 SLPM, respectively, through two nozzles provided in the section in which the liquid medium rose in the external down-corner. The continuous supply circulated the liquid medium at a rate of 4 L/min and chlorination of the vinyl chloride monomer proceeded. The reaction was carried out continuously under the conditions of 40° C. and 1 bar.

Test Example

While performing the reaction according to the above example, a product was collected at hourly intervals from 3 hours to 8 hours after the initiation of the reaction. At this time, the product was taken from the top (front; where descending of liquid medium begins) and the bottom (rear; where descending of liquid medium ends) of the external down-corner, respectively.

A concentration (mol/L) of 1,1,2-trichloroethane contained in each of the products collected was measured and is shown in Table 1 below.

TABLE 1

| Down-corner | Concentration of 1,1,2-trichloroethane (mol/L) | | | | | |
|---|---|---|---|---|---|---|
| | 3 hours | 4 hours | 5 hours | 6 hours | 7 hours | 8 hours |
| Top | 2.24 | 2.91 | 3.25 | 3.78 | 4.21 | 4.58 |
| Bottom | 2.26 | 2.94 | 3.44 | 4.01 | 4.44 | 4.77 |

Referring to Table 1, the concentration of 1,1,2-trichloroethane was higher in the sample collected at the bottom (rear) than the sample collected at the top (front) of the external down-corner over time. As a result, it was confirmed that sufficient contact and residence time may be secured while passing through the external down-corner to allow the chlorination of the vinyl chloride monomer, and thus continuous chlorination is possible.

DESCRIPTION OF SYMBOLS

| 100: Reaction unit | 10: Gas-lift type of bubble column |
|---|---|
| 20: External down-corner | 150: Distillation column |

The invention claimed is:

1. A process for producing 1,1,2-trichloroethane, comprising a step of
    obtaining a product containing 1,1,2-trichloroethane by an addition reaction of a dissolved vinyl chloride monomer and dissolved chlorine in contact with each other under a liquid medium comprising a chlorinated hydrocarbon-based solvent and iron(III) chloride as a catalyst suspended therein,
    wherein the step is carried out in a reaction unit comprising a gas-lift type of bubble column through which the liquid medium is circulated without a separate pump by gas containing the dissolved vinyl chloride monomer and dissolved chlorine and an external down-corner which circulates the gas and liquid medium out of the bubble column,
    wherein the addition reaction takes place in both the bubble column and the external down-corner,
    wherein the vinyl chloride monomer and chlorine are respectively supplied to a section in which the liquid medium rises in the gas-lift type of bubble column,
    wherein the step is carried out at a reaction temperature of 25 to 80° C.

2. The process for producing 1,1,2-trichloroethane of claim 1,
    wherein the chlorinated hydrocarbon-based solvent comprises at least one compound selected from the group consisting of carbon tetrachloride, chloroform, 1,2-dichloroethane, methylene chloride, trichloroethylene, 1,1,1-trichloroethane, 1,1,2-trichloroethane, and tetrachloroethylene.

3. The process for producing 1,1,2-trichloroethane of claim 1,
    wherein the catalyst comprises 100 to 1000 ppm of iron(III) chloride.

4. The process for producing 1,1,2-trichloroethane of claim 1,
    wherein a volumetric flow ratio of vinyl chloride monomer to chlorine ranges 1:1 to 1:0.8.

5. The process for producing 1,1,2-trichloroethane of claim 1,
    further comprising a step of recovering 1,1,2-trichloroethane by distilling the product containing 1,1,2-trichloroethane.

* * * * *